(12) United States Patent
Huang et al.

(10) Patent No.: US 8,747,879 B2
(45) Date of Patent: *Jun. 10, 2014

(54) METHOD OF FABRICATING AN IMPLANTABLE MEDICAL DEVICE TO REDUCE CHANCE OF LATE INFLAMMATORY RESPONSE

(75) Inventors: Bin Huang, Pleasanton, CA (US); David C. Gale, San Jose, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 1259 days.

This patent is subject to a terminal disclaimer.

(21) Appl. No.: 11/444,596

(22) Filed: May 31, 2006

(65) Prior Publication Data

US 2007/0253999 A1 Nov. 1, 2007

Related U.S. Application Data

(63) Continuation-in-part of application No. 11/413,220, filed on Apr. 28, 2006.

(51) Int. Cl.
*A61F 2/82* (2013.01)
*A61F 2/06* (2013.01)

(52) U.S. Cl.
USPC ............ 424/422; 424/423; 424/426; 623/1.1; 623/1.15; 623/1.38; 623/1.49

(58) Field of Classification Search
None
See application file for complete search history.

(56) References Cited

U.S. PATENT DOCUMENTS

| | | |
|---|---|---|
| 3,687,135 A | 8/1972 | Stroganov et al. |
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |

(Continued)

FOREIGN PATENT DOCUMENTS

| | | |
|---|---|---|
| DE | 44 07 079 | 9/1994 |
| DE | 197 31 021 | 1/1999 |

(Continued)

OTHER PUBLICATIONS

Answers.com blow molding; [online]; retrieved from the Internet on Feb. 27, 2009; retrieved from: http://www.answers.com/blow%20molding#Stretch_blow_molding; 4 pages.*
U.S. Appl. No. 10/317,435, filed Dec. 11, 2002, Hossainy et al.
Anonymous, *Bioabsorbable stent mounted on a catheter having optical coherence tomography capabilities*, Research Disclosure, Sep. 2004, pp. 1159-1162.
Ansari, *End-to-end tubal anastomosis using an absorbable stent*, Fertility and Sterility, vol. 32(2), pp. 197-201 (Aug. 1979).
Ansari, *Tubal Reanastomosis Using Absorbable Stent*, International Journal of Fertility, vol. 23(4), pp. 242-243 (1978).
Bull, *Parylene Coating for Medical Applications*, Medical Product Manufacturing News 18, 1 pg. (Mar. 1993).

(Continued)

*Primary Examiner* — Ernst Arnold
(74) *Attorney, Agent, or Firm* — Squire Sanders (US) LLP

(57) ABSTRACT

The invention provides a method for fabricating an implantable medical device to increase biocompatibility of the device, the method comprising: heat setting a polymer construct, wherein the polymer construct is at a temperature range of from about Tg to about $0.6(Tm-Tg)+Tg$ such that the set polymer construct comprises a crystalline structure having crystals at a size less than about 2 microns; and fabricating an implantable medical device from the heat set polymer construct.

10 Claims, 3 Drawing Sheets

(56) References Cited

U.S. PATENT DOCUMENTS

| | | |
|---|---|---|
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,010,445 A | 1/2000 | Armini et al. |
| 6,015,541 A | 1/2000 | Greff et al. |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,150,630 A | 11/2000 | Perry et al. |
| 6,153,252 A | 11/2000 | Hossainy et al. |
| 6,159,951 A | 12/2000 | Karpeisky et al. |
| 6,160,084 A | 12/2000 | Langer et al. |
| 6,165,212 A | 12/2000 | Dereume et al. |

(56) References Cited

U.S. PATENT DOCUMENTS

| | | | |
|---|---|---|---|
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,045 B1 | 2/2001 | Fehring et al. |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,273,913 B1 | 8/2001 | Wright et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,511,748 B1 | 1/2003 | Barrows |
| 6,517,888 B1 | 2/2003 | Weber |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,585,755 B2 | 7/2003 | Jackson et al. |
| 6,592,614 B2 | 7/2003 | Lenker et al. |
| 6,592,617 B2 | 7/2003 | Thompson |
| 6,613,072 B2 | 9/2003 | Lau et al. |
| 6,626,939 B1 | 9/2003 | Burnside et al. |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,689,375 B1 | 2/2004 | Wahlig et al. |
| 6,695,920 B1 | 2/2004 | Pacetti et al. |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,505 B1 | 7/2004 | Hossainy et al. |
| 6,818,063 B1 | 11/2004 | Kerrigan |
| 6,846,323 B2 | 1/2005 | Yip et al. |
| 7,066,952 B2 | 6/2006 | Igaki |
| 7,070,615 B1 | 7/2006 | Igaki |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0062148 A1 | 5/2002 | Hart |
| 2002/0065553 A1 | 5/2002 | Weber |
| 2002/0111590 A1 | 8/2002 | Davila et al. |
| 2002/0116050 A1 | 8/2002 | Kocur |
| 2002/0138133 A1 | 9/2002 | Lenz et al. |
| 2002/0161114 A1 | 10/2002 | Gunatillake et al. |
| 2003/0033001 A1 | 2/2003 | Igaki |
| 2003/0093107 A1 | 5/2003 | Parsonage et al. |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0171053 A1 | 9/2003 | Sanders |
| 2003/0187495 A1 | 10/2003 | Cully et al. |
| 2003/0208259 A1 | 11/2003 | Penhasi |
| 2003/0209835 A1 | 11/2003 | Chun et al. |
| 2003/0226833 A1 | 12/2003 | Shapovalov et al. |
| 2003/0236563 A1 | 12/2003 | Fifer |
| 2004/0093077 A1 | 5/2004 | White et al. |
| 2004/0098095 A1 | 5/2004 | Burnside et al. |
| 2004/0111149 A1 | 6/2004 | Stinson |
| 2004/0126481 A1 | 7/2004 | Weber |
| 2004/0143317 A1 | 7/2004 | Stinson et al. |
| 2004/0167610 A1 | 8/2004 | Fleming, III |
| 2004/0181271 A1 | 9/2004 | DeSimone et al. |
| 2005/0149172 A1 | 7/2005 | Varma |
| 2007/0142903 A1 | 6/2007 | Dave |
| 2007/0200271 A1 | 8/2007 | Dave |

FOREIGN PATENT DOCUMENTS

| | | |
|---|---|---|
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| GB | 2 102 827 | 2/1983 |
| GB | 2 247 696 | 3/1992 |
| JP | 49-036597 | 4/1974 |
| JP | 10-113384 | 5/1998 |
| JP | 2000-060956 | 2/2000 |
| JP | 2000-084064 | 3/2000 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 98/22157 | 5/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |

(56) References Cited

FOREIGN PATENT DOCUMENTS

| WO | WO 03/034940 | * | 5/2003 | ............... A61F 2/00 |
| --- | --- | --- | --- | --- |
| WO | WO 2004/023985 | | 3/2004 | |
| WO | WO 2005/096992 | | 10/2005 | |

OTHER PUBLICATIONS

Casper et al., *Fiber-Reinforced Absorbable Composite for Orthopedic Surgery*, Polymeric Materials Science and Engineering, vol. 53 pp. 497-501 (1985).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Devanathan et al., *Polymeric Conformal Coatings for Implantable Electronic Devices*, IEEE Transactions on Biomedical Engineering, vol. BME-27(11), pp. 671-675 (1980).

Elbert et al., *Conjugate Addition Reactions Combined with Free-Radical Cross-Linking for the Design of Materials for Tissue Engineering*, Biomacromolecules, vol. 2, pp. 430-441 (2001).

Hahn et al., *Biocompatibility of Glow-Discharge-Polymerized Films and Vacuum-Deposited Parylene*, J Applied Polymer Sci, vol. 38, pp. 55-64 (1984).

Hahn et al., *Glow Discharge Polymers as Coatings for Implanted Devices*, ISA, pp. 109-111 (1981).

He et al., *Assessment of Tissue Blood Flow Following Small Artery Welding with an Intraluminal Dissolvable Stent*, Microsurgery, vol. 19(3), pp. 148-152 (1999).

Kelley et al., *Totally Resorbable High-Strength Composite Material*, Advances in Biomedical Polymers, vol. 35, pp. 75-85 (1987).

Kubies et al., *Microdomain Structure in polylactide-block-poly(ethylene oxide) copolymer films*, Biomaterials, vol. 21, pp. 529-536 (2000).

Kutryk et al., *Coronary Stenting: Current Perspectives*, a companion to the Handbook of Coronary Stents, pp. 1-16 (1999).

Martin et al., *Enhancing the biological activity of immobilized osteopontin using a type-1 collagen affinity coating*, J. Biomed. Mater. Res., vol. 70A, pp. 10-19 (2004).

Mauduit et al., *Hydrolytic degradation of films prepared from blends of high and low molecular weight poly(DL-lactic acid)s*, J. Biomed. Mater. Res., vol. 30, pp. 201-207 (1996).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. Arter. Dis., vol. 1(4), pp. 438-448 (Jul./Aug. 1990).

Nichols et al., *Electrical Insulation of Implantable Devices by Composite Polymer Coatings*, ISA Transactions, vol. 26(4), pp. 15-18 (1987).

Peuster et al., *A novel approach to temporary stenting: degradable cardiovascular stents produced from corrodible metal-results 6-18 months after implantation into New Zealand white rabbits*, Heart, vol. 86, pp. 563-569 (2001).

Pietrzak et al., *Bioabsorbable Fixation Devices: Status for the Craniomaxillofacial Surgeon*, J. Craniofaxial Surg., vol. 2, pp. 92-96 (1997).

Pietrzak et al., *Bioresorbable implants—practical considerations*, Bone, vol. 19, No. 1, Supplement Jul. 1996, pp. 109S-119S.

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, vol. 79(2), pp. 445-457 (Feb. 1989).

Schmidt et al., *Long-Term Implants of Parylene-C Coated Microelectrodes*, Med & Biol Eng & Comp, vol. 26(1), pp. 96-101 (Jan. 1988).

Spagnuolo et al., *Gas 1 is induced by VE-cadherin and vascular endothelial growth factor and inhibits endothelial cell apoptosis*, Blood, vol. 103, pp. 3005-3012 (2004).

Tamai et al., *Initial and 6-Month Results of Biodegradable Poly-l-Lactic Acid Coronary Stents in Humans*, Circulation, pp. 399-404 (Jul. 25, 2000).

Tsuji et al., *Biodegradable Polymeric Stents*, Current Interventional Cardiology Reports, vol. 3, pp. 10-17 (2001).

Völkel et al., *Targeting of immunoliposomes to endothelial cells using a single-chain Fv fragment directed against human endoglin (CD105)*, Biochimica et Biophysica Acta 1663, pp. 158-166 (2004).

Van Vlack, *Elements of Materials Science and Engineering*, University of Michigan, pp. 270-271, 1989, 4 pgs.

Von Recum et al., *Degradation of polydispersed poly(L-lactic acid) to modulate lactic acid release*, Biomaterials, vol. 16, pp. 441-445 (1995).

Yau et al., Modern Size-Exclusion Liquid Chromatography, Wiley-Interscience Publication, IX-XV (1979).

Amendment and Response to OA of Feb. 4, 2009, for U.S. Appl. No. 11/413,220, 11 pgs.

Notice of Reasons for Rejection from JPO for Appl. No. P2009-513274, mailed Feb. 28, 2012, 5 pgs.

Translation of Notice of Reasons for Rejection from JPO for Appl. No. P2009-513274, mailed Feb. 28, 2012, 6 pgs.

* cited by examiner

METHOD OF FABRICATING AN IMPLANTABLE MEDICAL DEVICE TO REDUCE CHANCE OF LATE INFLAMMATORY RESPONSE

CROSS REFERENCE

This is a continuation in part of application Ser. No. 11/413,220 entitled, "Method of Fabricating an Implantable Medical Device by Controlling Crystalline Structure," filed Apr. 28, 2006.

BACKGROUND OF THE INVENTION

1. Field of the Invention

This invention relates to a method of fabricating an implantable medical device by controlling crystalline structure.

2. Description of the State of the Art

This invention relates generally to implantable medical devices having a range of mechanical and therapeutic requirements during use. In particular, the invention relates to radially expandable endoprostheses that are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty. "Restenosis" refers to the reoccurrence of stenosis in a blood vessel or heart valve after it has been subjected to angioplasty or valvuloplasty.

The stent must be able to satisfy several mechanical requirements. First, the stent must be capable of withstanding the structural loads, namely radial compressive forces, imposed on the stent as it supports the walls of a vessel lumen. This requires a sufficient degree of strength and rigidity or stiffness. In addition to having adequate radial strength, the stent should be longitudinally flexible to allow it to be maneuvered through a tortuous vascular path and to enable it to conform to a deployment site that may not be linear or may be subject to flexure. The material from which the stent is constructed must allow the stent to undergo expansion upon deployment which typically requires substantial deformation of portions of the stent. Once expanded, the stent must maintain its size and shape throughout its service life despite the various forces that may come to bear thereon, including the cyclic loading induced by the beating heart. Therefore, a stent must be capable of exhibiting relatively high toughness which corresponds to high strength and rigidity, as well as flexibility.

A stent is typically composed of scaffolding that includes a pattern or network of interconnecting structural elements or struts. The stent can be formed from wires, tubes, or sheets of material rolled into a cylindrical shape. A pattern can be formed in a tube, for example, by laser cutting. The scaffolding is designed to allow the stent to be radially expandable. The pattern is generally designed to maintain the longitudinal flexibility and radial rigidity required of the stent. Longitudinal flexibility facilitates delivery of the stent and radial rigidity is needed to hold open a bodily lumen upon deployment.

A medicated stent may be fabricated by coating the surface of either a metallic or polymeric scaffolding with a polymeric carrier that includes a bioactive agent. Polymeric scaffolding may also serve as a carrier of a bioactive agent.

In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode after the clinical need for them has ended.

One of the major problems associated with all types of stents is late inflammation caused by the stent after the stent begins to degrade and bioabsorb within the body. Inflammation may follow stent bioabsorption.

What is needed in the art is an implantable medical device and method for making the device that reduces the likelihood for late inflammation during bioabsorption as well as maintains mechanical requirements during treatment.

SUMMARY

The invention provides a method for fabricating an implantable medical device to increase biocompatibility of the device, the method comprising: heat setting a polymer construct, wherein the polymer construct is at a temperature range of from about Tg to about $0.6(Tm-Tg)+Tg$ such that the set polymer construct comprises a crystalline structure having crystals at a size less than about 2 microns; and fabricating an implantable medical device from the heat set polymer construct.

The invention also provides a method for fabricating an implantable medical device to increase biocompatibility, the method comprising: maintaining a polymer construct at a temperature greater than Tg of the polymer at which the crystal nucleation rate of the polymer construct is greater than the crystal growth rate such that crystals of the polymer construct at a size less than about 2 microns is obtained; and fabricating an implantable medical device from the heat set polymer construct.

The invention also provides an implantable medical device comprising: a plurality of crystalline domains having crystals dispersed within an amorphous domain, the majority of the crystals being less than about 2 microns.

Finally, the invention provides a method of treating a bodily lumen with a degradable stent comprising: disposing a degradable semicrystalline polymeric stent within a bodily lumen, wherein a majority of the crystals in the polymer are of a crystal size less than about 2 microns; and radially expanding the device within the lumen.

DETAILED DESCRIPTION

Figure 1:
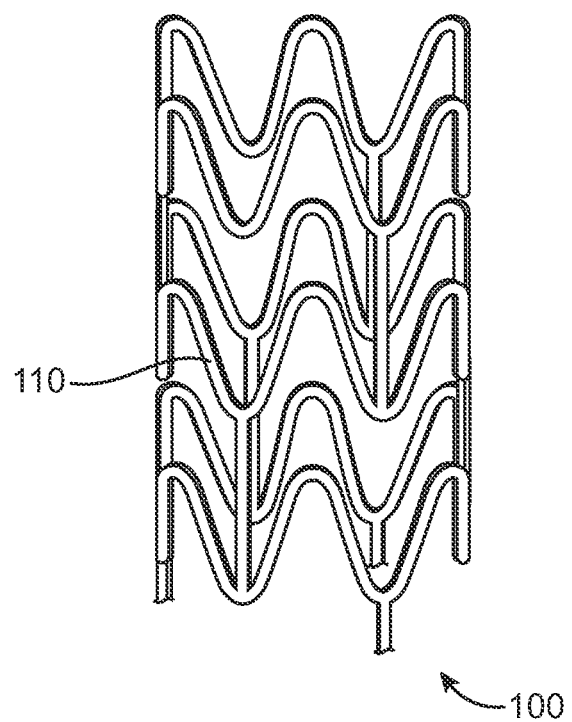
FIG. 1 depicts a three-dimensional view of a stent.

The embodiments of the present invention relate to implantable medical devices and methods to control the relationship between degree of nucleation and associated crystal growth to improve mechanical properties such as strength and flexibility, as well as increase the biocompatibility of the device by reducing chance of inflammation upon bioabsorption of the device.

For the purposes of the present invention, the following terms and definitions apply:

"Macrophage" is a relatively long-lived phagocytic cell of mammalian tissue, derived from blood monocyte.

"Polymer construct" refers to any useful article of manufacture made of a polymer such as a semi-crystalline polymer, or blend of polymers, any useful article of manufacture made of any material that is coated with a polymer or blend of polymers. Some examples of polymer constructs include, but are not limited to, a tube, a sheet, a fiber, etc.

"Glass transition temperature," $T_g$, is the temperature at which the polymer's amorphous domains transform from a brittle vitreous state to a solid deformable or ductile state at atmospheric pressure. In other words, the $T_g$ corresponds to the temperature where segmental motion starts in the polymer chains. When an amorphous or semicrystalline polymer is exposed to an increasing temperature, both the polymer's coefficient of expansion and the heat capacity increase as the temperature is raised, indicating increased molecular motion. As the temperature is raised, the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

"Toughness" is the amount of energy absorbed prior to fracture, or equivalently, the amount of work required to fracture a material. One measure of toughness is the area under a stress-strain curve from zero strain to the strain at fracture. The units of toughness are energy per unit volume of material. See, e.g., L. H. Van Vlack, "Elements of Materials Science and Engineering," pp. 270-271, Addison-Wesley (Reading, Pa., 1989).

A brittle material is a relatively stiff or rigid material that exhibits little or no plastic deformation. As stress is applied to a brittle material, it tends to fracture at a stress approximately equal to its ultimate strength, undergoing little or no plastic deformation in the process. A polymer below its Tg tends to be brittle. In contrast, a ductile material under an applied stress exhibits both elastic and plastic deformation prior to fracture. Above its Tg, a polymer is ductile.

A fracture may be categorized as either ductile or brittle. A relatively low amount of energy is required to fracture brittle materials. Conversely, ductile materials can absorb a relatively high amount of energy prior to fracture. Therefore, ductile materials tend to exhibit higher toughness than brittle materials. Toughness is a desirable characteristic in implantable medical devices.

The contrast between brittle fracture and ductile fracture is important in relation to an implantable medical device because it is useful in characterizing the device. The mechanical limits of an implantable medical device during use can be more accurately characterized by the amount of energy absorbed by the device rather than the strength of the device material. For example, two devices may be made of different materials having the same or similar ultimate strength. However, under the same conditions, a material with a lower toughness will fail before a material with a higher toughness.

As used herein, an "implantable medical device" refers to any type of appliance that is totally or partly introduced into a patient's body, and which is intended to remain there after the procedure. Examples of implantable medical devices include, without limitation, self-expandable stents, balloon-expandable stents, stent-grafts, implantable cardiac pacemakers and defibrillators; leads and electrodes for the preceding; implantable organ stimulators such as nerve, bladder, sphincter and diaphragm stimulators, cochlear implants, artificial bone; prostheses, vascular grafts, grafts, artificial heart valves and cerebrospinal fluid shunts. Of course, an implantable medical device specifically designed and intended solely for the localized delivery of a therapeutic agent is within the scope of this invention. The implantable medical device may be constructed of any biocompatible material.

FIG. 1 depicts a three-dimensional view of a stent 100. Stent 100 includes struts 110 that can take on a variety of patterns. The embodiments disclosed herein are not limited to stents or to the stent pattern illustrated in FIG. 1, but instead can be applied to other stent patterns and other devices.

As mentioned above, an implantable medical device may be configured to degrade after implantation by fabricating the device either partially or completely from biodegradable polymers. Polymers can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and may be gradually absorbed and eliminated by the body.

A biodegradable device may be intended to remain in the body until its intended function of, for example, maintaining vascular patency and/or drug delivery is accomplished. For biodegradable polymers used in coating applications, after the process of degradation, erosion, absorption has been completed, no polymer will remain on the stent. In some embodiments, very negligible traces or residue may be left behind. The duration is typically in the range of six to twelve months.

As the polymeric implantable medical device is bioabsorbed by the body, the amorphous phase is preferentially eroded compared to the discrete crystalline phase, leaving behind long-lasting crystals. In some cases, the degrading crystals cause undesirable effects in the body, such as inflammation, fibrosis, cell migration, cell proliferation, leukocyte activation, leukocyte adherence, lymphocyte activation, lymphocyte adherence, macrophage activation, macrophage adherence, cell death and neovascularization. Without being limited by theory, it is believed that the cellular response to the crystals is a function of crystal size. When crystal size is greater than around 2 microns, particularly greater than 10 microns, the likelihood that a late inflammatory reaction may occur during biodegradation of the stent is more likely. Several embodiments of a method are disclosed to reduce likelihood of inflammation by fabricating a stent such that when the stent biodegrades, smaller crystals of less than two microns are formed. When cells such as macrophages encounter smaller crystals of a size of less than 2 microns, for example, the crystals are digested with less chance of an inflammatory reaction Several embodiments of a method are disclosed for reducing crystal size in the implantable medical device, thereby reducing the likelihood of inflammation reaction, while still maintaining strength and flexibility of the device. Upon degradation, the device is made up of smaller crystals that readily undergo digestion by macrophages.

Representative examples of polymers that may be used to fabricate, coat, or modify an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(L-lactide-co-ε-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid).

Many polymers used for stent scaffoldings and coatings are relatively brittle and susceptible to mechanical instability at biological conditions. This is particularly true for polymers with a Tg above a body temperature, such as poly L-lactide ("PLLA"), where the polymer in the stent never reaches its Tg. As a result, PLLA has relatively low fracture toughness and a relatively low degradation rate at conditions within the human body. It is important for a device to have a high fracture toughness throughout the range of stress experienced during use of an implantable medical device.

Other potential problems with polymeric stents are creep, stress relaxation, and physical aging. Creep refers to the gradual deformation that occurs in a component subjected to an applied load. Creep occurs even when the applied load is constant. It is believed that the delayed response of polymer chains to stress during deformations causes of creep behavior. Deformation stops when the initially folded chains reach a new equilibrium configuration (i.e. slightly stretched). This deformation is recoverable after the load is removed, but recovery takes place slowly with the chains retracting by folding back to their initial state. The rate at which polymers creep depends not only on the load, but also on temperature. In general, a loaded component creeps faster at higher temperatures. Long term creep in a polymeric stent reduces the effectiveness of a stent in maintaining a desired vascular patency. In particular, long term creep allows inward radial forces to permanently deform a stent radially inward.

Stress relaxation is also a consequence of delayed molecular motions as in creep. Contrary to creep, however, which is experienced when the load is constant, stress relaxation occurs when deformation (or strain) is constant and is manifested by a reduction in the force (stress) required to maintain a constant deformation.

Physical aging, as used herein, refers to the densification in the amorphous regions of a semi-crystalline polymer. Densification is the increase in density of a material or region of a material. Densification results from residual and applied stresses. As used herein, a "residual stress" includes, without limitation, the stress in a bulk polymer that is in a non-equilibrium thermodynamic state. Physical aging of semi-crystalline polymers that have glass transition temperatures ($T_g$) above their normal storage temperature, which, for the purposes of this invention is room temperature, i.e., from about 15° C. to about 35° C., occurs primarily through the phenomenon known as densification.

Densification occurs when a semi-crystalline polymer is cooled at a non-equilibrium rate from a temperature above its $T_g$ to a temperature below its $T_g$. Such is in fact normally what will occur in most industrial settings in that equilibrium cooling is very slow and would be considered economically impractical. The non-equilibrium cooling rate results in the polymer chains of the amorphous domains being trapped at non-optimal separation distances in the glassy state that forms when the temperature goes below $T_g$. The chains then attempt to achieve optimal separation by coordinated localized chain motion. Although the reordering of polymer chains do not result in chain ordering, that is, the formation of lamellae and crystallites, which would constitute crystallization, the effect on the bulk properties of the polymer is similar to that obtained when crystallization occurs, that is, the modulus of the polymer increases and concomitantly the polymer becomes more brittle. Thus, densification of a polymer initially selected for its toughness and elasticity could cause in-use failure of a construct made of or coated with the polymer when the polymer ages or densities and becomes brittle.

Some polymers, such as semi-crystalline polymers usually contain both amorphous and crystalline domains at temperatures below their melting point. Amorphous regions are those in which polymer chains are situated in an essentially random orientation. Crystalline domains are those in which polymer chains adopt an ordered orientation with segments of separate chains or of the same chain becoming essentially parallel to one another to form structures known as lamellae. Lamellae initially form from a point of nucleation, which normally is a speck of impurity in the liquid polymer. The formed lamellae then grow outward from the nucleation point to form larger, essentially spherical crystalline structures known as crystallites.

If the polymer includes inter- or inner-chain crystalline structures, (lamellae and spherulites), which are not capable of movement unless they melt the movement of polymer chains in the amorphous domains is reduced and the ability of the chains to densify is correspondingly lessened. For this reason, increasing the degree of crystallinity of a polymer reduces or even eliminates physical aging.

Increased crystallinity, however, can be an undesirable characteristic in polymer constructs in which high toughness is important, since increased crystallinity can confer increased brittleness in a polymer. Specifically, a polymer construct can be brittle in a temperature range of use of an implantable medical device. Thus, it would be desirable to fabricate a polymer construct that is sufficiently crystalline to mitigate densification, i.e., physical aging, while reducing or eliminating the changes in bulk properties that accompany increased crystallinity, such as increased brittleness. Various aspects of the present invention provide a device and a method of fabricating the device having high fracture toughness as well as sufficient crystallinity to reduce physical aging.

It is well known by those skilled in the art that molecular orientation or alignment of polymer chains in a polymer is a particularly important phenomenon that strongly influences bulk polymer properties such as fracture toughness. Orientation refers to the degree of alignment of polymer chains along a longitudinal or covalent axis of the polymer chains. For example, the strength along a particular direction in a polymer is higher when there is alignment of polymer chains along the direction. Molecular orientation along the preferred direction in a polymeric material may be induced by applying stress along the preferred direction. Generally, required strength along a particular direction can be induced in the polymer construct for use in fabricating an implantable medical device.

As mentioned, radial strength is an important characteristic of stents. Therefore, strength and orientation along a circumferential direction can be induced by radially expanding a tube for fabricating a stent. During radial expansion, stress induces orientation of polymer chains, and crystallization is induced by stress and oriented-induced mechanisms. By deforming or radially expanding a polymer, orientation of the polymer chains are induced. In a polymer construct formed in this manner, it may be important that the induced orientation is maintained such that the stent can retain the increased strength due to the induced orientation. It is desirable for the stent to be stable as well as have sufficient toughness at the temperatures of use, e.g., body temperature.

Since polymer chain alignment is a time and temperature dependent process, a highly oriented structure that is thermodynamically stable at a given temperature may not be formed instantaneously. Thus, the polymer construct may be formed over a period of time. Therefore, after deforming a polymer construct, the polymer construct may be heat set. "Heat setting" refers to allowing aligned polymer chains in the polymer construct to equilibrate towards the induced highly oriented structure at an elevated temperature.

Several methods and devices are provided to control crystalline structure to reduce likelihood of inflammation upon bioabsorption of the device, while still maintaining adequate strength and flexibility in the device. A polymeric material is heat set at the temperature range according to the invention to form a greater number of smaller sized crystalline domains as compared to polymeric material heat set at a temperature near Tm of the polymer. The greater number of smaller sized crystalline domains reduces likelihood of inflammation upon bioabsorption of the device after the device degrades.

In addition, the greater number of smaller sized crystalline domains acts as net points to keep molecular orientation and material stability of the polymer. A polymeric material having a greater number of smaller sized crystalline domains produces more tie molecules, or polymer chains that link crystalline domains, compared to a small number of larger-sized crystals. A material having a greater number of smaller sized crystalline domains exhibits higher fracture toughness and less brittleness.

A material having a greater number of smaller sized crystalline domains can be formed by controlling nucleation rate and crystal growth rate, both a function of temperature. Nucleation rate is the rate of formation of crystals. Crystal growth rate is the rate at which existing crystals grow. The invention provides controlling the temperature while heat setting the material such that the degree of nucleation is larger than the associated crystal growth rate. In this way, a polymeric material is formed having of a greater number of smaller sized crystalline domains, thereby reducing the likelihood of inflammation upon bioabsorption of the device when the device degrades.

Figure 2:
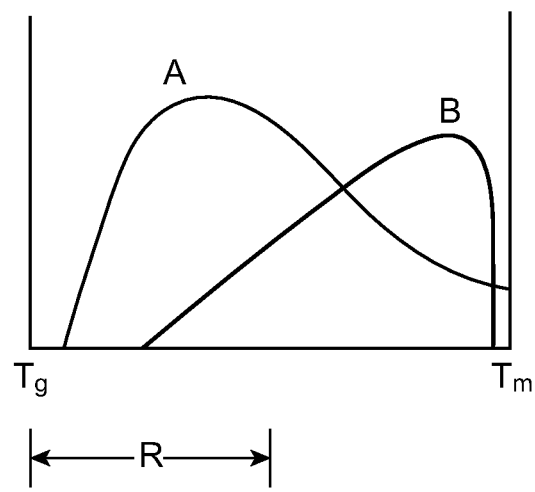
FIG. 2 depicts a graph illustrating the nucleation rate and growth rate of crystals in a polymer versus temperature of a polymer.

FIG. 2 is a graph of the nucleation rate A and crystal growth rate B as a function of temperature for a polymer is between, Tg and Tm. Polymer crystallization begins with nucleation, the formation of small crystalline domains that begin as specks of impurities in the amorphous liquid polymer. As depicted, the rate of nucleation A occurs most rapidly at temperatures near Tg. In contrast to the rate of nucleation A, crystal growth B occurs most rapidly at temperatures near Tm. At a temperature below Tg, there is no increase in crystal growth B or increase in crystallinity. As the temperature approaches Tm, crystal growth B increases logarithmically, at which point the crystals melt and the polymer chains resume an amorphous, completely random orientation.

The invention provides for heat setting a polymer construct, such that the temperature of the polymer construct allows a relatively high rate of nucleation coupled with a relatively low crystal growth rate (See R in FIG. 2 as a general indication of the temperature range at which heat setting of the polymer construct according to the invention takes place). Thus, the invention provides a method to control the relationship between degree of nucleation and associated crystal growth rate. At such temperature range, segmental motion of the polymer increases and polymer chains are able to orient and crystallize, and form a larger number of smaller-sized crystalline domains throughout the polymer construct.

During radial expansion and heat setting, crystallization is induced. Depending on the application of the polymer construct, a selected period of time to heat set the radially expanded polymer tube may be adjusted to achieve a given crystallinity. Further, the temperature at which the polymer construct is heat set may be varied within the temperature range according to the desired application of the polymer construct. Therefore, heat setting is performed in a temperature range that allows a larger number of small crystals, i.e., high nucleation rate and a low crystal growth rate, to achieve a desired circumferential strength and toughness for the stent.

The polymer construct is maintained at such a temperature range for a sufficient period of time to heat set the polymer construct. By "sufficient period of time" it is meant the time necessary to form an implantable medical device that can support a lumen in an expanded state for a treatment period. The resultant polymer construct yielded from this process has a crystallinity that is substantially formed of smaller crystalline domains. In addition, the number of crystalline domains in a polymer construct increases.

The polymer construct can be a blend of two or more polymers. The polymer construct may be, but is not limited to, a tube, sheet, fiber, or any other shape for use in fabricating an implantable medical device.

At a temperature of about Tg to about 0.6(Tm−Tg)+Tg, the polymer construct may be heat set at a temperature that allows a relatively greater nucleation rate A coupled with a relatively lower crystal growth rate B. Thus, the invention provides a method to control the relationship between degree of nucleation and associated crystal growth to reduce likelihood of inflammation upon bioabsorption of the device when the device degrades.

In addition, the polymer construct, prior to heat setting, may be deformed such that the temperature of the polymer construct is about Tg to about 0.6(Tm−Tg)+Tg and the set polymer construct comprises a crystalline structure having crystals at a size less than about 2 microns. At such temperature range, segmental motion of the polymer increases and polymer chains are able to orient and crystallize, forming a larger number of smaller-sized crystalline domains throughout the polymer construct. Consequently, physical aging, creep, and stress relaxation are reduced or curtailed if not eliminated. The relatively large number of small crystalline domains inhibits movement of chains in the amorphous domain.

During heat setting of the polymer construct, crystallization is induced. Heat setting is conventionally performed at temperatures near Tm, where nucleation rate is slow and crystal growth rate is fast, resulting in formation of fewer crystals of a larger size. Such a structure tends to cause late inflammation upon bioabsorption of the device.

In contrast, the method of the invention allows formation of smaller crystals by heat setting a polymer construct in a temperature range where nucleation rate A is relatively high, as depicted in FIG. 2, and crystal growth rate B is relatively low. Heat setting in this temperature range forms more crystalline domains of smaller size. Such a structure tends to reduce likelihood of inflammation upon bioabsorption of the device when the device degrades.

In certain embodiments, a method of fabricating an implantable medical device includes heat setting a polymer construct in a temperature range at which the crystal nucleation rate A is greater than the crystal growth rate B. In one embodiment, the crystal nucleation rate is greater than the crystal growth rate. In another embodiment, the crystal nucleation rate is substantially greater than the crystal growth rate. In one embodiment, the polymer construct is heat set while maintaining the polymer construct at a temperature range of from about Tg to about 0.6(Tm−Tg)+Tg. The polymer construct is heat set by maintaining the polymer construct at a temperature where the ratio of the crystal nucleation rate to crystal growth rate is 2, 5, 10, 50, 100, or greater than 100. The polymer construct is maintained at the selected temperature for a sufficient period of time to heat set the polymer construct. For example, the polymer construct may be maintained at a temperature range of from about Tg to about 0.6(Tm−Tg)+Tg. The heat set polymer construct may also be maintained at a temperature where the ratio of the crystal nucleation rate to crystal growth rate is 2, 5, 10, 50, 100, or greater than 100.

The polymer construct of the implantable medical device according to the invention may have any desired crystallinity according to the application of the device. At any given crystallinity, the polymer construct has a greater number of smaller sized crystalline domains.

Figure 4:
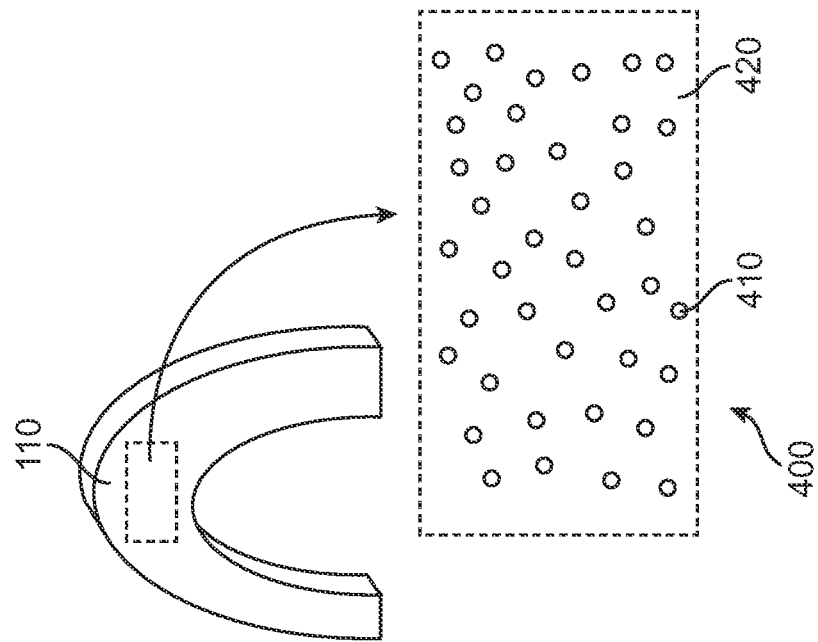
FIG. 4 depicts a schematic representation of the microstructure of a polymer tube deformed and heat set at temperatures closer to Tg than Tm according to the invention, having more crystals of smaller size compared to the polymer tube in FIG. 3, which is deformed and heat set at a temperature closer to Tm than Tg.
Figure 3:
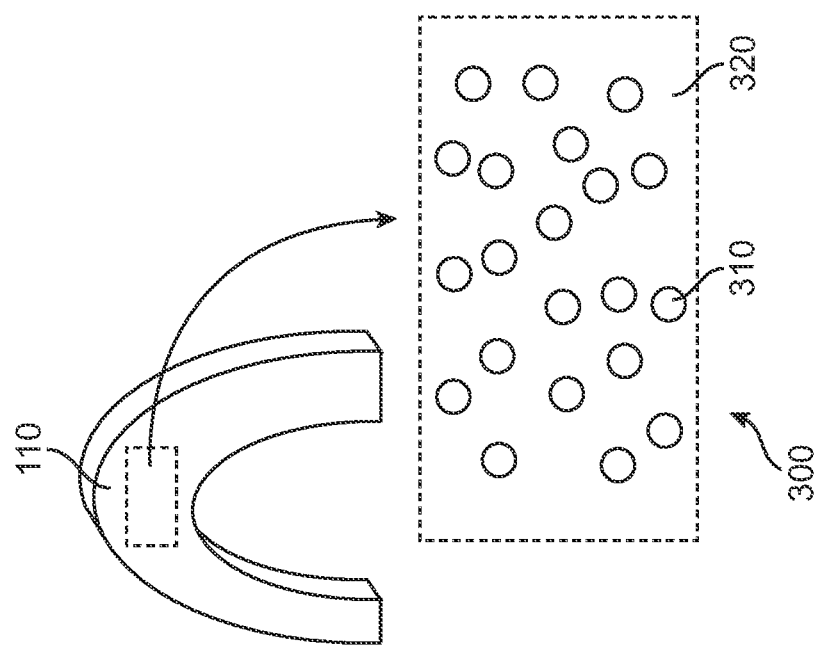
FIG. 3 depicts a schematic representation of the microstructure of a polymer tube deformed and heat set at temperatures closer to Tm than Tg, having fewer crystals of a larger size compared to the polymeric tube in FIG. 4, which is deformed and heat set at a temperature closer to Tg than Tm.

FIG. 3 depicts a blown up view of a portion 300 of a strut 110 (shown in FIG. 1) that has been deformed and heat set at a temperature closer to Tm than Tg, which has fewer larger-sized crystals or crystalline domains 310 dispersed in amorphous domain 320, as compared to FIG. 4, where portion 400 is deformed and heat set at a temperature closer to Tg than Tm. Portion 300 includes crystals 310 of a larger size because deformation and heat setting of polymer construct occurs at a temperature closer to Tm than Tg, where the crystal growth rate is substantially larger than the nucleation rate. Crystalline domains 310 are of a larger size, and thus, fewer crystalline domains are formed. In FIG. 3, crystalline domains 310 are larger compared to those in portion 400. Thus, the regions of the amorphous domain between crystalline domains in portion 300 are larger.

FIG. 4 depicts a blown up view of a portion 400 of a strut 110 that has been heat set at a temperature closer to Tg according to the invention. Portion 400 has a greater number of smaller crystalline domains 410, compared with portion 300 that is heat set at a temperature closer to Tm than Tg. Crystalline domains 410 and amorphous domains 420 of portion 400 are smaller in size. By heat setting the polymer construct according to the invention for a selected period of time, the size of the crystals can range from less than 10, less than 6, less than 2, or less than 1 micron.

Because amorphous domains 420 of portion 400 are constrained by the greater number of crystalline domains 410, the capacity for movement in the amorphous domains 420 of portion 400 is decreased. The shorter the distance between crystalline domains 410, the more the crystalline domains are able to constrain movement of regions of the amorphous domain 420. Crystalline domains 410 are able to exert more influence on the regions of the amorphous domain 420 surrounding crystalline domains 410 because the crystalline domains constrain movement of regions of the amorphous domain 420. The crystalline domains 410 or nucleation sites serve as "tie molecules" within amorphous domain 420 that tie the crystalline domains together, thereby locking crystalline domains into place so that movement of chains in the amorphous domains of the polymer construct is reduced. For this reason, portion 400 of the invention has smaller regions of amorphous domain 420 that resist physical aging, molecule creeping, and stress relaxation of portion 400.

In addition to controlling the physical aging of the polymer construct, the dimensional stability and brittleness of a polymer construct may be controlled. Because crystalline domains or net points serve as "tie molecules" within the amorphous domain that tie the crystalline domains together, thereby forming a tighter network of crystals that lock the crystalline domains into place, the mechanical properties of the polymer construct are improved. For example, both fracture toughness and shape stability of the polymer construct is increased. A tighter network of crystals is formed, and the possibility of fracturing is substantially reduced because cracks are forced to propagate through and around the many discrete crystals in the polymer construct. It is believed that the smaller and greater number of crystalline domains dispersed throughout the amorphous domain absorb energy due to crack propagation.

The polymer construct such as a tube, sheet, or fiber, may be deformed using methods and devices known to persons of skill in the art. For example, a polymer tube may be deformed by radially expanding and/or axially deforming the polymer construct. As discussed above, radial expansion of the polymer tube can induce circumferential molecular orientation which can increase circumferential strength and modulus or rigidity in the polymer tube. The polymer tube may be expanded radially by application of radial pressure. For example, the polymer tube may be expanded by blow molding.

Orientation of polymer chains may be induced by deformation along the axis of deformation. Small crystalline domains serve as net points to constrain polymer chains in the amorphous domain of portion. The motion of the polymer chains is restricted through the high number of small crystalline domains. A greater number of smaller-sized crystals can drastically restrict polymer chain motion in the amorphous domain while retaining desirable bulk properties of the polymer, such as toughness.

As mentioned above, since the polymer tube are heat set in a temperature range of high nucleation rate and slow crystal growth rate, orientation of the polymer chains are better maintained by the large number of small crystalline domains.

In one embodiment, the invention provides for heat setting by maintaining the deformed polymer construct in the deformed state at a temperature range of from about Tg to about 0.6(Tm−Tg)+Tg such that the set polymer construct comprises a crystalline structure having crystals at a size less than about 2 microns. It may be desirable to heat set the polymer construct at a temperature higher than the deformation temperature to increase the rate of the rearrangement of polymer chains. For example, in one embodiment, the polymer construct can be heat set at a temperature of about Tg to about 0.6(Tm−Tg)+Tg to allow polymer chains. The polymer may be maintained in the deformed state by maintaining a radial pressure and axial tension in the tube.

After heat setting, the polymer tube may then be cooled to below its Tg either before or after decreasing the pressure and/or decreasing tension. Cooling the polymer construct helps insure that the tube maintains the proper shape, size, and length following its formation. Upon cooling, the deformed polymer construct retains the length and shape imposed by an inner surface of the mold.

In one embodiment, the polymer construct consists essentially of semi-crystalline poly(L-lactic acid) or "PLLA". The glass transition temperature of PLLA is between 60° C. to about 100° C. The polymer construct of PLLA may be made by deforming the polymer construct between about Tg to about 0.6(Tm−Tg)+Tg, and maintaining the deformed polymer construct in the deformed state to heat set the polymer construct at a temperature range from about Tg to about 0.6(Tm−Tg)+Tg. In some embodiments, the polymer construct consisting essentially of PLLA is from about 45% to about 55% crystalline after deforming and heat setting the polymer construct. In one embodiment, percent crystallinity achieved for poly(L-lactide) is from about 5% to about 60%. In certain embodiments, the polymer construct consists essentially of PLLA and is made by deforming the polymer construct at a temperature in which the crystal nucleation rate is substantially greater than the crystal growth rate.

Various embodiments of the polymer construct described above may be used to fabricate an implantable medical device, such as a stent. As indicated above, a stent can be formed from a tube or a sheet rolled into a tube. A sheet or tube, for example, may by formed by various methods known in the art such as extrusion or injection blow molding.

Additionally, as indicated above, a stent fabricated from embodiments of the polymer construct described herein can be medicated with a bioactive agent. As used herein, a bioactive agent refers any substance that is of medical or veterinary therapeutic, prophylactic or diagnostic utility. Therapeutic use refers to a bioactive agent that, when administered to a patient, will cure, or at least relieve to some extent one or more symptoms of a disease or disorder. Prophylactic use refers to a bioactive agent that, when administered to a patient either prevents the occurrence of a disease or disorder or, if administered subsequent to a therapeutic agent, prevents or retards the recurrence of the disease or disorder. For the purposes of this invention, any such agent may be included in the construct that is subjected to the method so long as the conditions of the method will not adversely affect the agent.

This invention has been described in relation to certain examples of its application, such as its applicability to constructs comprising semi-crystalline PLLA. The examples are not intended nor should they be construed as limiting this invention in any manner. Those skilled in the art will recognize, based on the disclosures herein, other polymer and other constructs to which the invention herein may be applied. All such polymers and constructs are within the scope of this invention.

What is claimed is:

1. A method for fabricating an implantable medical device to reduce late inflammation upon bioabsorption of the device, the method comprising:
    radially expanding a polymer tube at a first temperature greater than a Tg of the polymer of the polymer tube, wherein the radial expansion induces crystallization in the polymer; and
    heat setting the expanded polymer tube while maintaining the tube in the expanded state, wherein the polymer tube is at a second temperature in the range of from Tg to 0.6(Tm−Tg)+Tg such that the heat set polymer tube comprises a crystalline structure having crystals at a size less than 2 microns or about 2 microns; and
    fabricating the implantable medical device which is a stent from the heat set polymer tube, wherein the fabricating comprises forming a pattern in the heat set polymer tube by cutting which forms a scaffolding including interconnecting structural elements.

2. The method according to claim 1, wherein the polymer tube comprises a crystalline structure having crystals at a size less than 1 micron or about 1 micron.

3. The method according to claim 1, wherein the polymer tube comprises poly(L-lactic acid).

4. The method according to claim 3, wherein the percent crystallinity of the poly(L-lactic acid) of the polymer tube after heat setting is from about 45% to about 55%.

5. The method according to claim 3, wherein the expanding and heating are done at a temperature of from 60° C. to 100° C.

6. A method for fabricating an implantable medical device to reduce late inflammation upon bioabsorption of the device, the method comprising:
    radially expanding a polymer tube at a first temperature greater than a Tg of the polymer of the polymer tube;
    wherein the radial expanding increases strength of the polymer, induces crystallization in the polymer, and induces circumferential orientation in the polymer around the polymer tube,
    maintaining the polymer tube in the radially expanded state at a second temperature greater than the Tg of the polymer at which the crystal nucleation rate of the polymer is greater than the crystal growth rate such that crystals of the polymer at a size less than 2 microns or about 2 microns are obtained which maintains the increased strength, induced circumferential orientation, and increases the fracture toughness of the polymer; and
    fabricating the implantable medical device which is a stent from the polymer tube after maintaining the polymer tube, wherein the fabricating comprises forming a pattern in the heat set polymer tube by cutting which forms a scaffolding including interconnecting structural elements.

7. The method according to claim 6, wherein crystals of the polymer at a size less than 1 micron or about 1 micron are obtained.

8. The method according to claim 6, wherein the second temperature is in a range of from Tg to 0.6(Tm−Tg)+Tg.

9. The method according to claim 6, wherein the polymer tube comprises poly(L-lactic acid), and the first and second temperatures are between 60° C. and 100° C.

10. The method according to claim 6, wherein the first temperature is in a range of from Tg to 0.6(Tm−Tg)+Tg.

* * * * *

UNITED STATES PATENT AND TRADEMARK OFFICE
CERTIFICATE OF CORRECTION

| | | Page 1 of 1 |
|---|---|---|
| PATENT NO. | : 8,747,879 B2 | |
| APPLICATION NO. | : 11/444596 | |
| DATED | : June 10, 2014 | |
| INVENTOR(S) | : Huang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1431 days.

Signed and Sealed this
Eighth Day of September, 2015

Michelle K. Lee
*Director of the United States Patent and Trademark Office*